United States Patent [19]
Kano et al.

[11] 3,948,926
[45] Apr. 6, 1976

[54] O,O-DIETHYL-2-(5-ETHYL-6-BROMOTHIAZOLO[3,2-b]-s-TRIAZOLYL)THIONOPHOSPHATE

[76] Inventors: Saburo Kano, No. 1968-3, Sohi, Odawara, Kanagawa; Osami Nomura, No. 2800, Kofuzu, Odawara, Kanagawa; Mitsuo Asada, No. 9-27, Tanjogaoka, Hiratsuka, Kanagawa; Meiki Ando, No. 1-56-6, Azuma-cho, Oisomachi, Naka, Kanagawa; Michihiko Matsuda, No. 25, Kokufuhongo, Oisomachi, Naka, Kanagawa; Tomio Yamada, No. 358, Tokunobu, Hiratsuka, Kanagawa; Hitoshi Watanabe, No. 845-1, Manda, Hiratsuka, Kanagawa; Takuzo Taniguchi, No. 8-11, Inamuragasaki 2-chome, Kamakura, Kanagawa, all of Japan

[22] Filed: Oct. 10, 1974

[21] Appl. No.: 513,861

Related U.S. Application Data

[60] Division of Ser. No. 386,020, Aug. 7, 1973, which is a continuation-in-part of Ser. No. 319,490, Dec. 29, 1972, Pat. No. 3,904,639.

[30] Foreign Application Priority Data

Dec. 30, 1971  Japan.................................. 46-3186

[52] U.S. Cl..... 260/306.7 E; 260/306.7 T; 424/200
[51] Int. Cl.$^2$........................................ C07D 513/04
[58] Field of Search 260/306.7 E, 256.4 E, 256.5 R, 260/302 E; 424/200

[56] References Cited
UNITED STATES PATENTS

| | | | |
|---|---|---|---|
| 3,518,279 | 6/1970 | Miller | 260/302 E |
| 3,657,247 | 4/1972 | Freeman et al. | 260/256.5 R |
| 3,682,943 | 8/1972 | Hoffmann et al. | 260/306.7 E |
| 3,840,541 | 10/1974 | Colln et al. | 260/256.5 R |

*Primary Examiner*—R. J. Gallagher
*Attorney, Agent, or Firm*—George B. Oujevolk

[57] ABSTRACT

A compound represented by the formula

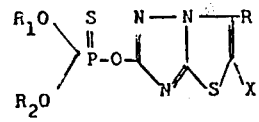

wherein
R, $R_1$ and $R_2$ are lower alkyl having six or less carbon atoms;
X is halogen.

1 Claim, No Drawings

O,O-DIETHYL-2-(5-ETHYL-6-BROMO-THIAZOLO[3,2-B]-S-TRIAZOLYL)THIONOPHOSPHATE

This is a division of Ser. No. 386,020, filed Aug. 7, 1973, which in turn is a continuation-in-part of Ser. No. 319,490, filed Dec. 29, 1972, now U.S. Pat. No. 3,904,639.

This invention relates to novel thiazolotriazolylphosphonothioates and to a process for the preparation of the same. Further, the invention relates to insecticidal and acaricidal compositions containing one or more of said novel compounds and further includes methods for combatting insects and mites with same compounds.

A number of organo phosphate insecticides have been used for the control of many injurious insects and certain materials are known to be effective. However, many of these systemic insecticides have a strong toxicity for human and warm-blooded animals.

Phytophagous mites are particularly harmful to plants, fruit trees and crops. The damage done is very large and large sums for extermination are spent annually. Further, some insects and mites have developed resistance against the currently used insecticides and acaricides. Therefore, it becomes a matter of importance to control the insects and the mites. Accordingly, development of novel, effective insecticides and acaricides are intensively desired in order to control these insects and mites.

The inventors have discovered that the compounds of this invention have superior insecticidal and acaricidal activities.

The novel compounds of this invention are characterized by the following formula:

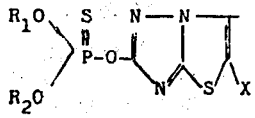

Wherein
R, $R_1$ and $R_2$ are lower alkyl having six or less carbon atoms,
X is halogen.

It is one object of the present invention to provide new thiazolotriazolylphosphonothioates, which are useful in the control of insects and mites. It is another object of the present invention that the compounds of the invention have sufficient low phyto-toxicity to use without any injury on living plants and extremely low mammalian toxicity.

In the Japanese Pat. No. 30192/1971 it has been shown that O,O-dialkyl-2-thiazolo[3,2-b]-s-triazolylthionophosphates having no substituent at 6 position therein shown are useful as insecticidal and acaricidal compositions.

The present inventors synthesized various thiazolotriazolylphosphonothioates and tested the biological activity thereof, and have discovered that thiazolotriazolylphosphonothioates having at the 6 position a substituent such as halogen have strong insecticidal and acaricidal activities and furthermore, these compounds have very low mammalian toxicity.

For example, the acute oral toxicity $LD_{50}$ (mouse) of O,O-diethyl-2-(5-methylthiazolo[3,2-b]-s-triazolyl)thionophosphates of Japanese Pat. No. 30192/1971 is 33–50 mg/kg, but in the case of O,O-diethyl-2-(5-methyl-6-bromothiazolo[3,2-b]-s-triazolyl)thionophosphate of the present invention it is 150 mg/kg, and furthermore for O,O-dialkyl-2-(5-ethyl-6-bromothiazolo [3,2-b]-s-triazolyl)thionophosphate it is more than 200 mg/kg, so that it is a safe agent.

The compounds of this invention can be prepared in accordance with the following equation:

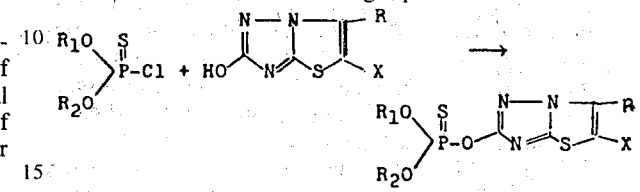

(wherein R, $R_1$, $R_2$ and X represent the aforesaid meanings.)

Usually the process of the invention is carried out in a proper inert solvent by the use of alkali condensing agents. As an inert solvent, acetone, dioxane, acetonitrile and pyridine have been employed as yet. Using these inert solvents, the compounds of this invention are obtained in low yield such as 5 to 6%.

However, inventors have discovered that the compounds of this invention are obtained in satisfactory high yields such as 50 to 70% when dimethylformamide or dimethylsulfoxide are employed as solvents in the presence of potassium carbonate or sodium carbonate as condensing agents.

In practical method the compounds of this invention are prepared through the reaction of O,O-dialkylthiophosphorylchloride with 6-halogenothiazolo[3,2-b]-s-triazol using dimethylformamide or dimethylsulfoxide as a solvent in the presence of alkali carbonate as condensing agent, or with alkali metal salts of 6-halogenothiazolo[3,2-b]-s-triazol which are dissolved in the solvent such as dimethylformamide or dimethylsulfoxide.

Reaction temperature is 40° – 60°C, preferably 45° – 50°C and the reaction terminates between 4 and 10 hours.

After the reaction is terminated, the products are isolated from the reaction mixture by employing the following treatment.

The reaction mixture is poured into water after cooling the mixture to the room temperature, this water mixture is alkalized by adding dilute sodium hydroxide solution and unreacted starting materials are dissolved in the alkali solution. The crystallized material was gathered by filtration, washed with water and dried, the crude product is obtained as a crystal.

The crude product can be purified by recrystallizing from a mixture of ligroin and petroleum ether.

The objective product is obtained as white crystal.

Unreacted starting material can be recovered from the mother liquor acidified with hydrochloric acid solution.

In order to facilitate a clear understanding or the invention, the following preferred specific embodiments are described as illustrative and not as limiting the invention.

EXAMPLE 1.

O,O-Dimethyl-2-(5-methyl-6-bromothiazolo[3,2-b]-s-triazolyl)thionophosphate 4.68 g of 2-hydroxy-5-methyl-6-bromothiazolo[3,2-b]-s-triazole, 3 g of potassium carbonate and 3 g of O,O-dimethylthiophosphoryl chloride were dissolved in 100 ml of dimethylformamide and heated at 45° – 50°C for 4 hours under agitation. Then the reaction mixture was poured into water and alkalized sodium hydroxide solution to crystallize the reaction product. The crystallized material was gathered by filtration, washed with water and dried. The dried crystal was recrystallized from mixed solvent of ligroin and petroleum ether and 4.1 g of white crystal having a melting point of 100° – 102°C were obtained. The crystal consist of O,O-dimethyl-2-(5-methyl-6-bromothiazolo[3,2-b]-s-triazolyl)thionophosphate, and the elemental analysis was as follows:

Found (%); C, 23.41 ; H, 2.55 ; N, 11.95 ; S, 17.64 ; Calcd. for $C_7H_9BrN_3O_3PS_2$ (%) ; C, 23.47 ; H, 2.53 ; N, 11.73 ; S, 17.90.

EXAMPLE 2.

O,O-Diethyl-2-(5-methyl-6-bromothiozolo[3,2-b]-s-triazolyl)thionophosphate 4.86 g of 2-hydroxy-5-methyl-6-bromothiazolo[3,2-b]-s-triazole, 3 g of potassium carbonate and 3.4 g of O,O-diethylthiophosphoryl chloride were dissolved in 100 ml of dimethylformamide and heated at 45° – 50°C for 4 hours under agitation.

By a procedure similar to Example 1, 5 g of O,O-diethyl-2-(5-methyl-6-bromothiazolo[3,2-b]-s-triazolyl)thionophosphate having a melting point of 102° – 103°C were obtained. Elemental analysis was as follows:

Found (%) ; C, 27.83 ; H, 3.47 ; N, 11.11 ; S, 16.22 ; Calcd. for $C_9H_{13}BrN_3O_3PS_2$ (%) ; C, 27.99 ; H, 3.39 ; N, 10.88 ; S, 16.60.

EXAMPLE 3.

O,O-Dimethyl-2-(5-methyl-6-chlorothiazolo[3,2-b]-s-triazolyl)thionophosphate 3.79 g of 2-hydroxy-5-methyl-6-chlorothiazolo[3,2-b]-s-triazole, 3 g of potassium carbonate and 3 g of O,O-dimethylthiophosphoryl chloride were dissolved in 100 ml of dimethylformamide and healed at 45° – 50°C for 4 hours under agitation.

By a procedure similar to Example 1, 3.4 g of O,O-dimethyl-2-(5-methyl-6-chlorothiazolo[3,2-b]-s-triazolyl)thionophosphate having a melting point of 73° – 75°C were obtained. Elemental analysis was as follows:

Found (%) ; C, 26.71 ; H, 2.94 ; N, 13.67 ; S, 20.34 ; Calcd. for $C_7H_9ClN_3O_3PS_2$ (%) ; C, 26.80 ; H, 2.89 ; N, 13.39 ; S, 20.44.

EXAMPLE 4.

O,O-Diethyl-2-(5-methyl-6-chlorothiazolo[3,2-b]-s-triazolyl)thionophosphate 3.79 g of 2-hydroxy-5-methyl-6-chlorothiazolo[3,2-b]-s-triazole, 3 g of potassium carbonate and 3.4 g O,O-diethylthiophosphoryl chloride were dissolved in 100 ml of dimethylformamide and heated at 45° – 50°C for 4 hours under agitation.

By a procedure similar to Example 1, 4.5 g of O,O-diethyl-2-(5-methyl-6-chlorothiazolo[3,2-b]-s-triazolyl)thionophosphate having a melting point of 80° – 82°C were obtained. Elemental analysis was as follows:

Found (%) ; C, 31.54 ; H, 3.78 ; N, 12.76 ; S, 18.54 ; Calcd. for $C_9H_{13}ClN_3PS_2$ (%) ; C, 31.63 ; H, 3.83 ; N, 12.30 ; S, 18.76.

In addition to the above mentioned compound described in the preceding examples, some typical compounds of the present invention are listed in Table I.

EXAMPLE 5.

O,O-Dimethyl 2-(5-ethyl-6-bromothiazolo[3,2-b]-s-triazolyl) thionophosphate

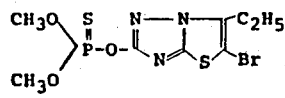

3.1 g of 2-hydroxy-5-ethyl-6-bromothiazolo[3,2-b]-s-triazole, 1 g of potassium carbonate and 2.1 g of O,O-dimethylthionophosphoryl chloride were dissolved in 15 ml of dimethylformamide and heated at 35° – 40°C for 4 hours under agitation. Then the reaction mixture was poured into water and alkalized sodium hydroxide solution to crystallize the reaction product. The crystallized material was gathered by filtration, washed with water and dried. The dried crystal was recrystallized from n-hexane and 3.35 g of white needle having a melting point of 55° – 56°C were obtained. The crystal consist of O,O-dimethyl 2-(5-ethyl-6-bromothiazolo[3,2-b]-s-triazolyl)thionophosphate, and the elemental analysis was as follows:

Found(%): C 25.63, H 2.75, N 11.00, S 17.21, Pr 21.74, P 8.18; calcd. for $C_8H_{11}N_3O_3S_2BrP$(%): C 25.80, H 2.95, N 11.29, S 17.74, Br 21.50, P 8.33.

EXAMPLE 6.

O,O-Diethyl 2-(5-ethyl-6-bromothiazolo[3,2-b]-s-triazolyl) thionophosphate

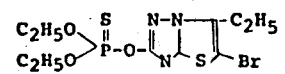

3.1 g of 2-hydroxy-5-ethyl-6-bromothiazolo[3,2-b]-s-triazole, 1 g of potassium carbonate and 2.32 g of O,O-diethylthionophosphoryl chloride were dissolved in 15 ml of dimethylformamide and heated at 40° – 50°C for 4 hours under agitation.

By a procedure similar to Example 1, 4.0 g of white needle O,O-diethyl 2-(5-ethyl-6-bromothiazolo[3,2-b]-s-triazotyl)thionophosphate having a melting point of 67° – 68°C (ligroin) were obtained. Elemental analysis was as follows;

Found(%): C 29.79, H 3.91, N 10.27, S 16.00, Br 20.11, P 7.79, Calcd. for $C_{10}H_{15}N_3O_3S_2BrP$(%): C 30.00, H 3.75, N 10.50, S 16.00, Br 20.00, P 7.75.

EXAMPLE 7.

O,O-diisopropyl 2-(5-ethyl-6-bromothiazolo[3,2-b]-s-triazolyl)thionophosphate

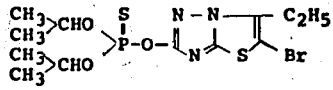

3.1 g of 2-hydroxy-5-ethyl-6-bromo[3,2-b]-s-triazole, 1 g of potassium carbonate and 2.97 g of O,O-diisopropylthionophosphoryl chloride were dissolved in 15 ml of dimethylformamide and heated at 40° – 45°C for 3 hours under agitation.

By a procedure similar to Example 1, 4.01 g of white needle O,O-diisopropyl 2-(5-ethyl-6-bromo-thiazolo[3,2-b]-s-triazolyl)thionophosphate having a melting point of 50° – 51°C were obtained. Elemental analysis was as follows;

Found (%): C 33.70, H 4.71, N 9.82, S 15.00, Br 18.64, P 7.04; Calcd. for $C_{12}H_{19}N_3O_3S_2BrP$(%): C 33.64, H 4.43, N 9.81, S 14.95, Br 18.69, P 7.24.

In addition to the above mentioned compound described in the preceding examples, some typical compounds of the present invention are listed in Table I.

Table 1

| Compound | R | $R_1$ | $R_2$ | X | m.p.(°C) |
|---|---|---|---|---|---|
| I | $CH_3$ | $CH_3$ | $CH_3$ | Br | 100 – 120°C |
| II | $CH_3$ | $C_2H_5$ | $C_2H_5$ | Br | 102 – 103°C |
| III | $CH_3$ | $CH_3$ | $CH_3$ | Cl | 73 – 75°C |
| IV | $CH_3$ | $C_2H_5$ | $C_2H_5$ | Cl | 80 – 82°C |
| V | $CH_3$ | $CH_3$ | $C_2H_5$ | Br | 93 – 95°C |
| VI | $C_2H_5$ | $CH_3$ | $CH_3$ | Br | 55 – 56°C |
| VII | $C_2H_5$ | $C_2H_5$ | $C_2H_5$ | Br | 67 – 68°C |
| VIII | $C_2H_5$ | $(CH_3)_2CH$ | $(CH_3)_2CH$ | Br | 50 – 51°C |

Hereinafter, the compounds of this invention are represented by Compound No. in Table 1.

The method of the present invention comprehends the employment of a liquid or solid composition containing one or more of the present compounds as an active component.

The compound can be used directly without mixing with suitable carriers.

The active ingredient of this invention may be formulated by mixing with suitable carriers in a form generally used in pesticidal composition such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, xylene, cyclohexane, cyclohexanone, dimethylformamide, dimethylsulfoxide, alcohol, acetone, benzene and others are used. Sometimes surface active agent is added in order to give a homogeneous and stable formulation.

Furthermore, the composition may be applied as a mixture with other fungicides, insecticides, acaricides, plant growth regulators and fertilizers.

The concentrations of the active ingredients in the insecticidal and acaricidal compositions of this invention vary according to type of formulation, and they are, for example, used in a range of 5 – 80 weight percent, preferably 20 – 80 weight percent, in wettable powders, 5 – 70 weight percent, preferably 10 – 50 weight percent, in emulsifiable concentrates, and 0.5 – 20 weight percent, preferably 1 – 10 weight percent in dust formulations.

The non-limiting examples for the insecticidal and acaricidal compositions are illustrated as follows:

Example 5.

| Wettable Powder | Parts by weight |
|---|---|
| Compound 1 | 40 |
| Higher alcohol sulfonate ester | 5 |
| Diatomaceous earth | 51 |
| White carbon | 4 |

These are mixed homogeneously and micronized to fine particles. Consequently, wettable powder containing 40% of active ingredient is obtained. In practical use, it is diluted to a certain concentration with water and is sprayed as a suspension.

Example 6.

| Emulsifiable Concentrate | Parts by weight |
|---|---|
| Compound 2 | 30 |
| xylene | 40 |
| dimethylformamide | 22 |
| polyoxyethylene alkylarylether | 8 |

These are mixed and dissolved.

Consequently, emulsifiable concentrate containing 30% of the active ingredient is obtained. In practical use, it is diluted to certain concentration with water and then is sprayed as an emulsion.

Example 7

| Dust Formulation | Parts by weight |
|---|---|
| Compound 3 | 3 |
| Talc | 97 |

These are mixed homogeneously and micronized to fine particles. Consequently, dust formulation containing 3% of the active ingredient is obtained. In practical use it is directly applied.

In the Example 5 – 7, it is not intended to limit the emulsifying, wetting or dispersing agents, carriers and solvents to the ones described by way of illustration.

The compounds listed in Table 1 possess very superior insecticidal and acaricidal activities compared to known compounds.

The superior insecticidal and acaricidal effects of the novel compounds of this invention are clearly illustrated by the following tests.

In these all tests, O,O-dimethyl-2-(5-methyl-thiazolo[3.2-b]-s-triazolyl)thionophosphate of the Japanese Pat. No. 30192/1971 is compared with the compounds of this invention.

Test 1. Insecticidal Activity against Fly

Fixed concentration of acetone solution containing test compound were prepared.

Twenty house flies (Musca domestica Linne) were tested with 1 l of acetone solution at their thoracic dorsal by microcylinge and kept at a temperature of 25°C and at a humidity of 65%. 24 hours and 48 hours after treatment, dead flies were counted and mortality (%) was calculated. The results were shown in Table 2.

Table 2

| Test Compound | Active compound 1γ/1 fly 24 hrs. | 48 hrs. | active compound 0.5γ/1 fly 24 hrs. | 48 hrs. |
|---|---|---|---|---|
| I | 100 | 100 | 95 | 100 |
| II | 100 | 100 | 90 | 100 |
| III | 100 | 100 | 90 | 95 |
| IV | 100 | 100 | 90 | 100 |
| V | 100 | 100 | 90 | 100 |
| Contrast* | 100 | 100 | 70 | 70 |

| Test Compound | active compound 0.5 γ/1 fly | | active compound 0.25 γ/1 fly | |
|---|---|---|---|---|
| | 24 hrs. | 48 hrs. | 24 hrs. | 48 hrs. |
| VII | 100 | 100 | 30 | 40 |
| Contrast* | 70 | 70 | 0 | 10 |

*Contrast: O,O-diethyl-2-(5-methylthiazolo[3,2-b]-s-triazolyl)thionophosphate

Test 2. Insecticidal Activity against Cockroach

Acetone solution of test compound were dropped on filter paper having a diameter of 9cm in order that active compound on filter paper became 125 and 31.3mg/m². The filter paper was air-dried and setted in schale, and in which 10 hatched nymph (American cockroach, *Periplaneta americana* Linne) were inoculated.

24 hours and 72 hours after inoculation, dead insects were counted and mortality (%) was calculated.

The results were shown in Table 3.

Table 3

| Test Compound | Active compound 125 mg/m² | | Active compound 31.3 mg/m² | |
|---|---|---|---|---|
| | 24 hrs. | 72 hrs. | 24 hrs. | 72 hrs. |
| I | 100 | 100 | 30 | 100 |
| II | 100 | 100 | 100 | 100 |
| III | 100 | 100 | 40 | 100 |
| IV | 100 | 100 | 100 | 100 |
| V | 100 | 100 | 100 | 100 |
| Contrast* | 100 | 100 | 0 | 30 |

Test 3 Insecticidal Activity against Mosquito

An aqueous suspension of wettable powder formulated in similar manner to Example 5 were poured in 200 ml beaker and in which 20 Japanese celler mosquito (*Culex pipiens pallens* Coqvii Maskell) were inoculated. 24 hours and 48 hours after inoculation, dead mosquitos were counted and mortality (%) were calculated.

The results were shown in Table 4.

Table 4

| Conc. of Active Ingredient (ppm) | Test Compound No. II 24 hrs. | 48 hrs. | Contrast* 24 hrs. | 48 hrs. |
|---|---|---|---|---|
| 0.0833 | | | 100 | 100 |
| 0.0417 | | | 10 | 100 |
| 0.0209 | | | 0 | 30 |
| 0.0105 | | | 0 | 0 |
| 0.0083 | | | | |
| 0.0067 | 100 | 100 | | |
| 0.0042 | 100 | 100 | | |
| 0.0021 | 95 | 100 | | |
| 0.0011 | 15 | 90 | | |

Test 4. Insecticidal Activity against Aphid

A potted chrysanthemum which Chrysanthemum aphid (*Macrosiphoniella sanborni* Gillette) inhabiting and a potted apple which Woolly apple aphid (*Eriosoma lanigerum* Hausmann) inhabiting were used.

An aqueous suspension of wettable powder formulated in similar manner to Example 5 were sprayed. After fixed day from spraying, the inhabiting state of Aphid was observed and estimated according to following grading.

− : no effect
+ : weak effect
++ : considerable effect
+++ : nearly perfect effect The results were shown in Table 5.

Table 5

| Test Compound | Chrysanthemum aphid (Conc. of Active Ingredient 100 ppm) | | Woolly apple aphid (Conc. of Active Ingredient 500 ppm) | |
|---|---|---|---|---|
| | 7 days | 10 days | 7 days | 10 days |
| I | +++ | +++ | +++ | +++ |
| II | +++ | +++ | +++ | +++ |
| III | +++ | +++ | +++ | +++ |
| IV | +++ | +++ | +++ | +++ |
| V | +++ | +++ | +++ | +++ |
| Contrast* | +++ | +++ | ++ | +++ |

Test 5 Insecticidal Activity against Cabbage armyworm

10 Multigeneration breeded armyworms (*Leucania separata* Walker) were used for this test.

A leaf of corn plant was dipped in an aqueous emulsion of emulsifiable concentrate formulated in similar manner to Example 6 for 30 seconds and air dried. Then the leaf was setted on filter paper having 9 cm diameter in a schale. The test insects were inoculated into the schale and the schale was put on the cover. After 1 day and 3 days from inoculation, dead insects were counted and mortality (%) were calculated. The results were shown in Table 6.

Table 6

| Test Compound | Concentration 62.5 ppm | | Concentration 31.3 ppm | | Concentration 15.7 ppm | | Concentration 7.8 ppm | |
|---|---|---|---|---|---|---|---|---|
| | 1 day | 3 days | 1 day | 3 days | 1 day | 3 days | 1 day | 3 days |
| I | 100 | 100 | 100 | 100 | 90 | 100 | 60 | 100 |
| II | 100 | 100 | 100 | 100 | 100 | 100 | 80 | 90 |
| III | 100 | 100 | 100 | 100 | 80 | 100 | 50 | 90 |

Table 6-continued

| Test Compound | Concentration 62.5 ppm | | Concentration 31.3 ppm | | Concentration 15.7 ppm | | Concentration 7.8 ppm | |
|---|---|---|---|---|---|---|---|---|
| | 1 day | 3 days | 1 day | 3 days | 1 day | 3 days | 1 day | 3 days |
| IV | 100 | 100 | 90 | 100 | 80 | 100 | 50 | 90 |
| V | 100 | 100 | 100 | 100 | 90 | 100 | 70 | 100 |
| Contrast* | 90 | 100 | 70 | 100 | 30 | 80 | 0 | 0 |

| Test compound | Concentration 31.3 ppm | | Concentration 15.7 ppm | | Concentration 7.8 ppm | |
|---|---|---|---|---|---|---|
| | 1 day | 2 days | 1 day | 2 days | 1 day | 2 days |
| VI | 100 | 100 | 60 | 100 | 50 | 90 |
| VII | 100 | 100 | 90 | 100 | 60 | 100 |
| VIII | 100 | 100 | 60 | 100 | 50 | 90 |
| Contrast* | 70 | 100 | 30 | 80 | 0 | 0 |

Test 6 Test for Control of Mite

About 30 adult female mites of desert spider mite (*Tetranychus desertorum* Banks) laid on main leaves of the potted kidney bean plants grown 7 to 10 days stage after sprouting. One day later, the wounded mites were removed from the plants. The compounds to be tested were sprayed on the plants as water suspension of emulsifiable concentrate prepared by the method of Example 6. After 1 day and 3 days from spraying, dead mites were counted and mortality (%) was calculated. Rating of mortality was recorded as follows:

| Mortality | Rating |
|---|---|
| 100 % | +++ |
| 99 – 90 % | ++ |
| 89 – 50 % | + |
| 50 – 0 % | – |

The results are shown in Table 7.

Table 7

| Test Compound | Concentration of Active Ingredient | | | | | |
|---|---|---|---|---|---|---|
| | 125 ppm | | 31.3 ppm | | 7.81 ppm | |
| | 1 day | 3 days | 1 day | 3 days | 1 day | 3 days |
| I | +++ | | +++ | | +++ | |
| II | +++ | | +++ | | +++ | |
| III | +++ | | +++ | | +++ | |
| IV | +++ | | +++ | | +++ | |
| V | +++ | | +++ | | +++ | |
| Contrast* | +++ | | +++ | | ++ | +++ |

| Test compound | Concentration of active ingredient 500 ppm 3 days |
|---|---|
| VI | +++ |
| VII | +++ |

Table 7-continued

| Test Compound | Concentration of Active Ingredient | | | | | |
|---|---|---|---|---|---|---|
| | 125 ppm | | 31.3 ppm | | 7.81 ppm | |
| | 1 day | 3 days | 1 day | 3 days | 1 day | 3 days |
| Contrast* | | | +++ | | | |

Test 7 Insecticidal Activity against Rice stem borer 20 hatched nymph of Rice stem borer (*Chilo suppressalis* Walker) were inoculated to the potted rice (height: 30–40 cm, number: 4/pot). A week after inoculation, 30 ml of fixed concentration of solution containing test compound were sprayed on the rice in which hatched nymph were inhabiting and the pots were kept at room temperature. A week after spraying, the rice was opened, dead Rice stem borer were counted and mortality (%) was calculated.

The results were shown in Table 8.

Table 8

| Test compound | Mortality (%) | | |
|---|---|---|---|
| | Concentration 31.3 ppm | Concentration 15.6 ppm | Concentration 7.8 ppm |
| VII | 100 | – | 91 |
| Contrast* | 100 | 84 | – |

What is claimed is:

1. The compound of the formula

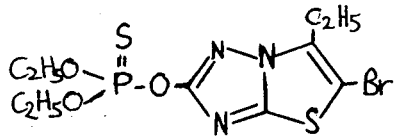

* * * * *